United States Patent [19]
Siegel et al.

[11] Patent Number: 6,127,580
[45] Date of Patent: Oct. 3, 2000

[54] PROCESS FOR THE PREPARATION OF SUBSTITUTED ANTHRAQUINONES

[75] Inventors: Wolfgang Siegel, Limburgerhof; Andreas Kramer, Freinsheim, both of Germany

[73] Assignee: BASF Aktiengesellschaft, Ludwigshafen, Germany

[21] Appl. No.: 09/200,936

[22] Filed: Nov. 30, 1998

Related U.S. Application Data

[62] Division of application No. 08/523,887, Sep. 6, 1995.

[30] Foreign Application Priority Data

Dec. 2, 1997 [DE] Germany ............... 197 53 484

[51] Int. Cl.[7] .................................................. C07C 45/00
[52] U.S. Cl. ............................................ 568/365; 568/317
[58] Field of Search .................................... 568/317, 365

[56] References Cited

U.S. PATENT DOCUMENTS

| | | | |
|---|---|---|---|
| 2,072,867 | 3/1937 | Carothers | 260/6 |
| 3,778,452 | 12/1973 | Josey et al. | 260/369 |
| 4,176,125 | 11/1979 | Matsuura et al. | 260/369 |
| 5,723,675 | 3/1998 | Joo et al. | 568/317 |

FOREIGN PATENT DOCUMENTS

| | | |
|---|---|---|
| 673825 | 4/1929 | France . |
| 1253697 | 4/1960 | France . |
| 2751662 | 5/1979 | Germany . |
| 59051235 | 9/1982 | Japan . |
| 57206633 | 12/1982 | Japan . |
| 58180452 | 10/1983 | Japan . |
| 320375 | 11/1929 | United Kingdom . |
| 884881 | 12/1961 | United Kingdom . |

OTHER PUBLICATIONS

*Bioorg. Med. Chem. Lett.*, 6, 1996, pp. 1859–1864.

Primary Examiner—Dwayne C. Jones
Attorney, Agent, or Firm—Keil & Weinkauf

[57] ABSTRACT

Process for the preparation of anthraquinones of the general formula I

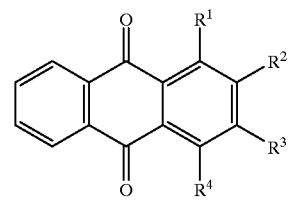

(I)

in which $R^1$, $R^2$, $R^3$ and $R^4$, which can be identical or different, are hydrogen, a $C_1$–$C_8$-alkyl or $C_2$–$C_8$-alkenyl radical, in which 1,4-naphthoquinone is reacted with a 1,3-diene of the general formula II

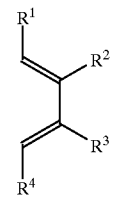

(II)

in a cycloaddition step to give the corresponding tetrahydroanthraquinone and the tetrahydroanthraquinone is oxidized with oxygen in the presence of a basic catalyst to give the anthraquinone, in which both the cycloaddition step and the oxidation step are carried out in the presence of an aqueous diluent.

Preferably, the cycloaddition step and oxidation step are carried out at a reaction temperature between 90 and 110° C. and at atmospheric pressure.

16 Claims, No Drawings

PROCESS FOR THE PREPARATION OF SUBSTITUTED ANTHRAQUINONES

This is a division of application Ser. No. 08/523,887, filed Sep. 6, 1995.

The invention relates to a process for the preparation of substituted anthraquinones.

It is known to prepare substituted 9,10-anthraquinones starting from 1,4-naphthoquinone and substituted 1,3-dienes. In this process, in a first synthesis step, 1,4-naphthoquinone is reacted with a substituted 1,3-diene in a cycloaddition reaction (Diels-Alder reaction) to give the substituted tetrahydroanthraquinone. In a second synthesis step, the oxidation of the substituted tetrahydroanthraquinone to give the substituted anthraquinone is carried out, it also being possible to carry out the oxidation stepwise via the substituted dihydroanthraquinone.

U.S. Pat. No. 2,072,867 describes the preparation of 9,10-anthraquinones, which are substituted in the 2-position by alkyl (methyl, butyl, heptyl) or phenyl, from 1,4-naphthoquinone and the appropriately substituted dienes isoprene, 2-butylbutadiene, 2-heptylbutadiene and 2-phenylbutadiene. The cycloaddition step is carried out at 90 to 100° C. in ethanol as a solvent or without use of an additional solvent. The substituted 1,4,4a,9a-tetrahydroanthraquinone obtained is then oxidized to the correspondingly substituted 9,10-anthraquinone in an alcoholic potassium hydroxide solution.

Working without solvents or diluents is accompanied by the serious disadvantage, that the heat of reaction cannot be dissipated effectively. Adequate mixing of the reaction components cannot be ensured either.

DE-A-21 50 337 describes the preparation of 1-alkenyl-9,10-anthraquinones, which can moreover also be substituted in the 2- and 3-position. In this process, 1,4-naphthoquinone and the correspondingly substituted 1,3,7-octatrienes are used as starting materials. The reaction should in this case be carried out in a solvent in which preferably at least one reactant, preferably both reactants, are soluble. Suitable solvents for carrying out the cycloaddition step mentioned in the specification are ketones such as acetone and methyl ethyl ketone, ethers such as THF and dioxane, alcohols such as methanol, ethanol and isopropanol, esters such as ethyl acetate and hydrocarbons such as benzene and cyclohexane. For carrying out the oxidation step, a suitable solvent mentioned in addition to those listed above is also water; a preferred medium is aqueous ethanol. A preferred temperature range indicated for carrying out the oxidation with atmospheric oxygen is 20 to 50° C. In the Examples, the cycloaddition step is carried out using ethanol or benzene as a solvent and the oxidation step using aqueous ethanol as a solvent, the atmospheric oxidation of the intermediate being carried out at room temperature or with ice-cooling.

JP 59-51235 describes the synthesis of 2-isohexenyl-9,10-anthraquinone from 1,4-naphthoquinone and myrcene, the oxidation of the intermediate being carried out with atmospheric oxygen. Both in the cycloaddition step and in the oxidation step, the reaction is carried out in ethanol as a solvent. A disadvantage in the use of ethanol or generally of alcohols as solvents is that these are not completely inert under the reaction conditions to oxidation by oxygen. This can lead to the formation of by-products which can make laborious purification operations necessary.

The atmospheric oxidation of the tetrahydroanthraquinone in the presence of readily volatile organic compounds such as low-boiling alcohols furthermore involves the risk of the formation of explosive mixtures of the readily volatile organic compounds and oxygen. Large-scale implementation of the process then has to be ruled out for safety reasons. The solvents used may be readily volatile organic compounds. Readily volatile organic compounds may also be contained in the starting components as minor constituents.

The danger of the formation of explosive mixtures can be countered on the one hand by using oxidants other than oxygen.

U.S. Pat. No. 5,723,675 describes a process for the preparation of anthraquinone from 1,4-naphthoquinone and butadiene, in which the reaction is carried out in DMSO as an oxidant and solvent. In the reduction of DMSO, products were formed which can act as catalyst poisons in the later use of anthraquinone in the $H_2O_2$ synthesis. The process is also laborious because of the extraction steps to be carried out.

Bioorg. Med. Chem. Lett. 6 (1996), pp. 1859–1864 discloses the synthesis of 2-isohexenyl-9,10-anthraquinone from 1,4-naphthoquinone and the terpene α-myrcene in diethyl ether as a solvent in the presence of a Lewis acid. The oxidation of the Diels-Alder adduct is carried out in the presence of oxidants such as $Ag_2O$, $MnO_2$ and DDQ in diethyl ether or benzene as a solvent. The oxidants and solvents used are expensive, physiologically unacceptable and therefore unsuitable for carrying out a large-scale process.

The danger of the formation of explosive mixtures can be avoided on the other hand by working in water as a reaction medium. The problem is that the starting components naphthoquinone and diene as well as intermediates and final products of the reaction are not readily soluble in water.

It is an object of the present invention to make available a synthesis process for anthraquinones which can be carried out on a large scale, starting from 1,4-naphthoquinone and 1,3-dienes, which is economical and uncomplicated in process technology terms and does not have the disadvantages of the processes known from the prior art, in particular to make available a process in which the danger of the formation of explosive gas mixtures in the oxidation step is avoided.

We have found that the object is achieved according to the invention by a process for the preparation of anthraquinones of the general formula I

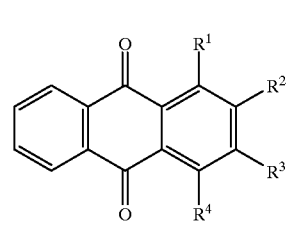

(I)

in which $R^1$, $R^2$, $R^3$ and $R^4$, which can be identical or different, are hydrogen, a $C_1$–$C_8$-alkyl or $C_2$–C8-alkenyl radical, in which 1,4-naphthoquinone is reacted with a 1,3-diene of the general formula II

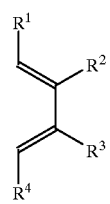

in which $R^1$, $R^2$, $R^3$ and $R^4$ have the meaning indicated above, in a cycloaddition step to give the corresponding tetrahydroanthraquinone and the tetrahydro-anthraquinone is reacted in an oxidation step with oxygen in the presence of a basic catalyst to give the anthraquinone of the general formula I, which comprises carrying out both the cycloaddition step and the oxidation step in the presence of an aqueous diluent.

Dienes in the sense of this invention are substituted 1,3-dienes as well as unsubstituted 1,3-butadiene. In addition to the alkyl or alkenyl-substituted derivatives, tetrahydroanthraquinones or anthraquinones are accordingly also the unsubstituted parent compounds.

An aqueous diluent in the sense of the invention is understood as meaning a diluent which mainly consists of water. Organic solvents miscible with water in small amounts can be contained in the aqueous diluent. Preferably, the amount of the organic solvents in the aqueous diluent is so small that under the reaction conditions the equilibrium vapor pressure of the organic solvents in the gas space above the reaction mixture is so small compared with the corresponding equilibrium vapor pressure that the formation of explosive gas mixtures can be ruled out. In general, this is the case when the content of the organic solvents in the aqueous diluent is <5% by weight. In a particularly preferred embodiment of the invention, the reaction is carried out exclusively with water as the aqueous diluent.

In a first synthesis step, 1,4-naphthoquinone is reacted with a 1,3-diene of the general formula I to give the tetrahydroanthraquinone. Preferably, the 1,3-dienes are present in the liquid phase under the reaction conditions, in particular at the reaction temperature demanded, at which the reaction to give the tetrahydroanthraquinone takes place. Preferred 1,3-dienes contain 4 to 24 C atoms, particularly preferably 5 to 12 C atoms, especially preferably 8 to 10 C atoms. Examples are isoprene, 2-ethyl-1,3-butadiene, 2-propyl-1,3-butadiene, 2-allyl-1,3-butadiene, 2-(3-buten-1-yl)-1,3-butadiene, 2-(4-penten-1-yl)-1,3-butadiene, 1,3-pentadiene, 1,3-hexadiene, 1,3-heptadiene, 1,3,6-heptatriene, 1,3,7-octatriene, 2- or 7-methyl-, 2- or 7-ethyl-, 2,7-dimethyl- or 2,7-diethyl-1,3,7-octatriene as well as terpene such as ocimene and myrcene. Of these, myrcene is particularly preferred.

The 1,4-naphthoquinone can also have substituents, for example alkyl substituents. Preferably, however, unsubstituted 1,4-naphthoquinone is employed.

When carrying out the cycloaddition step in the aqueous diluent, the starting components are in general present as a dispersion, that is as an emulsion, suspension or as a 3-phase mixture (solid/liquid/liquid), it also being possible for the aqueous diluent to contain small amounts of one or both starting components, even in dissolved form. Preferably, the starting components are selected such that after heating to the reaction temperature in the aqueous diluent at least one component is present in liquid form. If only one starting component is present in the liquid form, this can be the 1,3-diene or 1,4-naphthoquinone, preferably it is the 1,3-diene.

When carrying out the cycloaddition step, the reaction temperature is in general 50° C. to 170° C., preferably 70° C. to 130° C., particularly preferably 90 to I 10° C., and the reaction time is in general 0.5 to 24 h, preferably 3 to 12 h.

In a second synthesis step, the tetrahydroanthraquinone formed is oxidized to the anthraquinone of the general formula I in the presence of oxygen. In general, the tetrahydroanthraquinone is in this case present dispersed in the aqueous diluent.

Oxygen in pure form or in the presence of inert gases, for example in the form of air, can be employed. Preferably, atmospheric oxygen is employed as the oxidant.

The oxidation takes place in the presence of a basic compound soluble in the aqueous diluent. Suitable basic compounds are ammonia, sodium acetate, mono-, di- and trialkylamines, alkali metal and alkaline earth metal hydroxides. Preferably, the oxidation step takes place in the presence of a strongly basic compound such as an alkali metal or alkaline earth metal hydroxide, particularly preferably an alkali metal hydroxide. The basic compound employed is particularly sodium hydroxide.

In the oxidation step, oxygen is brought into contact intensively with the liquid reaction mixture. This can be achieved by passing the atmospheric oxygen—preferably in finely divided form—through the liquid reaction mixture. However, it can also be fed into the gas space above the reaction mixture and brought into contact with the reaction mixture by intensive stirring. The oxidation step is in general carried out at a temperature of from 20 to 170° C., preferably from 50 to 130° C., particularly preferably from 90° C. to 110° C. and during a period of 1 to 48 h, preferably 4 to 30 h.

Both the cycloaddition and the oxidation step can be carried out at normal pressure, reduced pressure or elevated pressure. In general, it is carried out at a pressure of from 0.5 to 30 bar. Working under elevated pressure is indicated if the reaction is to be carried out at temperatures far above the boiling point of water. This can be advantageous if high-melting substituted dienes are to be reacted. Working under elevated pressure is also indicated if a diene which is gaseous at atmospheric pressure—for example butadiene—is to be liquefied. In a preferred embodiment of the invention, the cycloaddition and oxidation step are carried out at normal pressure.

As a result of working in the presence of an aqueous diluent, the danger of the formation of explosive mixtures is avoided. On the one hand, this is already achieved by dispensing with organic solvents. Explosive gas mixtures may also be formed from oxygen and readily volatile organic compounds present in the starting components as minor constituents. This danger can be countered by setting a sufficiently high water vapor pressure and a low stationary oxygen concentration in the gas space above the reaction mixture. Water vapor pressure and stationary oxygen concentration above the reaction mixture can be adjusted without problems on heating under reflux by means of the heat supply, which determines the amount of refluxing distillate, and the oxygen supply.

The danger of the formation of explosive gas mixtures can also be countered by removing readily volatile minor constituents from the reaction mixture before carrying out the oxidation step. In the process according to the invention, this can be achieved particularly simply by incipient distillation (partial distillation) of the reaction mixture. In the case of incipient distillation, for example, about 20 to 30% by weight of the aqueous diluent employed is distilled off, readily volatile minor constituents being removed with the distillate. The aqueous diluent removed by distillation can be replaced during the distillation process - for example according to the steam distillation principle. The removal of the readily volatile minor constituents by incipient distillation or by steam distillation is possible without problems in the presence of an aqueous diluent. The removal of readily volatile minor constituents can be carried out before or after carrying out the cycloaddition step. In a preferred embodiment of the process according to the invention, it is carried out after carrying out the cycloaddition step.

After carrying out the oxidation step, the anthraquinone of the general formula I can be removed from the anthraquinone-containing emulsion formed. The anthraquinone can be removed in solid or in liquid form.

The anthraquinone of the general formula I can be removed in solid form. The anthraquinone can be removed by crystallization at low temperature and subsequent solid/liquid separation, for example by centrifugation or filtration. Customary steps for the purification of the crystallizate can follow the removal. Customary purification steps are, for example, recrystallization from an organic solvent. Before recrystallization, the crystallizate can be washed with a suitable solvent, for example water. The crystallizate removed can furthermore be fused and purified by distillation.

The anthraquinone of the general formula I can also be removed in liquid form. This can be achieved by extraction of the emulsion with an organic solvent. Removal in liquid form can also be achieved without addition of an organic solvent. In a preferred embodiment of the invention, the organic phase containing the anthraquinone is removed in liquid form from the emulsion formed after phase separation. The anthraquinone can be recovered from the removed organic phase by customary purification operations. Customary purification operations are the extraction of the removed organic phase with water, the distillation of the organic phase or the crystallization of the anthraquinone from an organic solvent. In a particularly preferred embodiment of the process according to the invention, the removed organic phase present in liquid form is washed with water and then distilled.

Using the process according to the invention, a product of sufficient purity can be obtained even without carrying out laborious purification steps. This is based on the one hand on the fact that water as a solvent is almost completely inert to oxidation by oxygen and the formation of impurities by oxidation of the solvent is excluded. On the other hand, by-products formed in the process according to the invention, for example those by-products which are formed by oxidation of olefinic double bonds in the intermediates or final products, are mainly water-soluble. As a result, these by-products concentrate in the aqueous phase and are largely removed with the aqueous phase after carrying out the oxidation step. Otherwise, the use of an aqueous diluent makes possible separation of the anthraquinones of the general formula I formed without problems after phase separation of the aqueous phase from the liquid organic phase containing the anthraquinone.

In a particularly preferred variant, the process according to the invention is carried out using the following steps:

a) 1,4-naphthoquinone, the diene of the general formula II and the aqueous diluent are introduced into a heatable reaction container, for example a stirring vessel.

b) 1,4-naphthoquinone and the diene of the general formula II are dispersed in the aqueous diluent, for example by stirring. Introduction of the starting components and dispersion can optionally be carried out under a protective gas atmosphere.

c) The dispersion, which can contain solid constituents, is heated to the reaction temperature under a protective gas atmosphere for the reaction of 1,4-naphthoquinone and of the diene of the general formula II. As a result of the heating, the diene melts and forms an emulsion in the aqueous diluent.

d) To remove readily volatile minor constituents, the emulsion formed containing the tetrahydroanthraquinone is subjected to incipient distillation. The removal of the readily volatile minor constituents is completed when about 20 to 30% by weight of the amount of water employed has passed over. This amount of water can be replaced during the distillation process, for example according to the steam distillation principle.

e) Alkali metal hydroxide is added to the reaction container, for example by introduction of an aqueous sodium hydroxide solution.

f) Atmospheric oxygen is introduced into the reaction container and reacted with the tetrahydroanthraquinone at about 90° C. The stationary oxygen concentration above the liquid reaction mixture is controlled via the heat supply and the oxygen supply such that the oxygen concentration in the gas space above the solution is at most 5% by volume.

g) After carrying out the oxidation step, phase separation of the emulsion is containing the anthraquinone of the general formula I into a liquid organic phase and an aqueous phase is brought about and the liquid organic phase is removed as a crude product. The purity of the crude product can be >97% by weight.

h) The liquid organic phase is subjected to customary purification steps to obtain the pure anthraquinone of the general formula I. Customary purification steps are, in particular, the extraction of the liquid organic phase with water. A distillation can follow. Purification can also be dispensed with.

The invention is illustrated in greater detail by the following examples.

EXAMPLE 1

180 l of water are introduced at room temperature into a stirring container with reflux cooling and 33.3 kg of 1,4-naphthoquinone and 40 kg of myrcene are fed in with stirring. The mixture is heated to 98 to 100° C. under a nitrogen atmosphere and stirred at this temperature for about 3 hours. The readily volatile components are then removed by incipient distillation of the reaction mixture. For the oxidation of the Diels-Alder adduct, 20 kg of a 25% strength aqueous NaOH solution are passed into the stirring container and the reaction mixture is aerated with atmospheric oxygen under reflux. The stationary oxygen concentration above the reaction mixture is controlled by means of the amount of distillate, which is adjusted by means of the heat supply, and the air supply. After the end of the oxidation, the mixture is cooled to room temperature, and the crude product crystallizes out and is removed. The synthesis yield is >94% of theory.

EXAMPLE 2

The procedure is as in Example 1, but after the oxidation the liquid organic phase is removed and then extracted at 90° C. with 180 l of water. The crude product which is liquid at 90 to 95° C. is then distilled by means of a wiper blade evaporator. The distillation yield is >90 %.

We claim:

1. A process for the preparation of anthraquinones of the general formula I

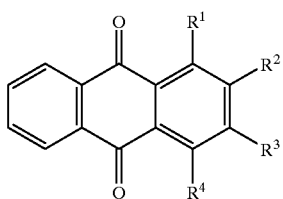 (I)

in which $R^1$, $R^2$, $R^3$ and $R^4$, which can be identical or different, are hydrogen, a $C_1$–$C_8$-alkyl or $C_2$–$C_8$-alkenyl radical, in which 1,4-naphthoquinone is reacted with a 1,3-diene of the general formula II

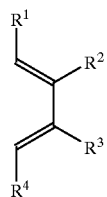 (II)

in which $R^1$, $R^2$, $R^3$ and $R^4$ have the meaning indicated above, in a cycloaddition step to give the corresponding tetrahydroanthraquinone and the tetrahydroanthraquinone is reacted in an oxidation step with oxygen in the presence of a basic catalyst to give the corresponding anthraquinone of the general formula I, which comprises carrying out both the cycloaddition step and the oxidation step in the presence of an aqueous diluent, in which the liquid and/or solid reactants and products are present as a dispersion.

2. The process as claimed in claim 1, wherein the cycloaddition step and oxidation step are carried out at a reaction temperature between 90 and 110° C.

3. The process as claimed in claim 1, wherein both the cycloaddition step and the oxidation step are carried out at atmospheric pressure.

4. The process as claimed in claim 1, wherein the readily volatile minor constituents present in the dispersion formed containing the tetrahydroanthraquinone are removed between the cycloaddition step and the oxidation step.

5. The process as claimed in claim 1, wherein after carrying out the oxidation step the organic phase is removed in liquid form after phase separation from the emulsion formed containing the substituted anthraquinone.

6. The process as claimed in claim 1, wherein the basic compounds employed are alkali metal hydroxides.

7. The process as claimed in claim 1, wherein the 1,3-diene employed is myrcene.

8. The process as claimed in claim 4, wherein after carrying out the oxidation step the organic phase is removed in liquid form after phase separation from the dispersion formed containing the substituted anthraquinone and the basic compounds employed are alkali metal hydroxides.

9. The process as claimed in claim 8 having the steps:

a) Introduction of 1,4-naphthoquinone, of the diene of the general formula II and of the aqueous diluent into a heatable reaction container;

b) Dispersion of 1,4-naphthoquinone and of the diene of the general formula II in the aqueous diluent;

c) Heating of the dispersion to the reaction temperature for the reaction of 1,4-naphthoquinone and of the substituted diene of the general formula II under a protective gas atmosphere;

d) Removal of readily volatile minor constituents, by incipient distillation (partial distillation) of the dispersion formed containing the substituted tetrahydroanthraquinone;

e) Addition of alkali metal hydroxide to the reaction container;

f) Introduction of atmospheric oxygen into the reaction container and reaction with the tetrahydroanthraquinone;

g) Phase separation of the dispersion formed containing the final product into a liquid organic phase and an aqueous phase and removal of the liquid organic phase;

h) optionally purification of the liquid organic phase to obtain the pure anthraquinone of the general formula I.

10. The process of claim 1, in which said aqueous diluent contains less than 5% by weight of organic solvents.

11. The process of claim 10, in which said aqueous diluent consists exclusively of water.

12. The process of claim 1, in which said dispersion is an emulsion in at least one of the two process steps.

13. The process of claim 1, in which said dispersion is a suspension in at least one of the two process steps.

14. The process of claim 1, in which said dispersion is a solid/liquid/liquid 3-phase mixture in at least one of the two process steps.

15. The process of claim 12, in which said dispersion is an emulsion in both of said process steps.

16. The process of claim 9, in which said dispersion is an emulsion in both of steps d) and g).

* * * * *